(12) United States Patent
Narita

(10) Patent No.: US 10,492,664 B2
(45) Date of Patent: Dec. 3, 2019

(54) ELECTRONIC ENDOSCOPE AND ELECTRONIC ENDOSCOPE DEVICE

(71) Applicant: FUJIFILM Corporation, Tokyo (JP)

(72) Inventor: Satoshi Narita, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 674 days.

(21) Appl. No.: 14/625,316

(22) Filed: Feb. 18, 2015

(65) Prior Publication Data

US 2015/0272426 A1 Oct. 1, 2015

(30) Foreign Application Priority Data

Mar. 27, 2014 (JP) ................................ 2014-066321

(51) Int. Cl.
*A61B 1/00* (2006.01)

(52) U.S. Cl.
CPC ................. *A61B 1/00124* (2013.01)

(58) Field of Classification Search
CPC ............ A61B 1/00112; A61B 1/00114; A61B 1/00124
USPC ........................................ 600/132, 110, 109
See application file for complete search history.

(56) References Cited

U.S. PATENT DOCUMENTS

| | | | | |
|---|---|---|---|---|
| 4,615,330 | A * | 10/1986 | Nagasaki | A61B 1/00177 128/901 |
| 4,853,772 | A * | 8/1989 | Kikuchi | H04N 5/2251 128/908 |
| 6,099,465 | A * | 8/2000 | Inoue | A61B 1/05 348/75 |
| 2004/0092793 | A1 | 5/2004 | Akai | |
| 2006/0116550 | A1 * | 6/2006 | Noguchi | A61B 1/121 600/132 |
| 2006/0116552 | A1 | 6/2006 | Noguchi et al. | |
| 2008/0039686 | A1 * | 2/2008 | Mori | A61B 1/00165 600/109 |

(Continued)

FOREIGN PATENT DOCUMENTS

| | | |
|---|---|---|
| CN | 1826079 A | 8/2006 |
| CN | 102573607 A | 7/2012 |

(Continued)

OTHER PUBLICATIONS

Chinese Office Action and Search Report, dated Feb. 27, 2017, for corresponding Chinese Application No. 201510062190.4 with an English translation of the Office Action.

(Continued)

*Primary Examiner* — Alexandra L Newton
*Assistant Examiner* — Rynae Boler
(74) *Attorney, Agent, or Firm* — Birch, Stewart, Kolasch & Birch, LLP

(57) ABSTRACT

There is provided an electronic endoscope and an electronic endoscope device with increased noise resistance. An electronic endoscope includes a connector that is connected to a processor device, and transmission and reception of electric power and signals are performed between the connector and the processor device. In the connector, an input and output portion for transmission and reception of electric power and signals is insulated from the processor device, and only a contact portion connected to a ground of the electronic endoscope is electrically connected to a ground of the processor device.

8 Claims, 4 Drawing Sheets

(56) References Cited

U.S. PATENT DOCUMENTS

2012/0202385 A1    8/2012   Miyagi et al.

FOREIGN PATENT DOCUMENTS

| JP | 10-155740 A | 6/1998 |
|----|----|----|
| JP | 2004-148028 A | 5/2004 |
| JP | 2013-208187 A | 10/2013 |
| WO | WO 2005/077250 A1 | 8/2005 |
| WO | WO 2011/052408 A1 | 5/2011 |

OTHER PUBLICATIONS

Japanese Office Action dated Mar. 8, 2016, for Japanese Application No. 2014-066321 with the English translation.
Chinese Office Action and English translation, dated Sep. 11, 2017, for corresponding Chinese Application No. 201510062190.4.
Chinese Office Action dated Mar. 22, 2018 for corresponding Chinese Application No. 201510062190.4, with English translation.

* cited by examiner

ELECTRONIC ENDOSCOPE AND ELECTRONIC ENDOSCOPE DEVICE

CROSS-REFERENCE TO RELATED APPLICATIONS

The present application claims priority under 35 U.S.C. § 119 to Japanese Patent Application No. 2014-066321, filed on Mar. 27, 2014. The above application is hereby expressly incorporated by reference, in its entirety, into the present application.

BACKGROUND OF THE INVENTION

1. Field of the Invention

The present invention relates to an electronic endoscope and an electronic endoscope device.

2. Description of the Related Art

An electronic endoscope in which an electronic device, such as an imaging device, is mounted is connected to a processor device, so that transmission and reception of electric power and signals between the electronic endoscope and the processor device are performed.

For the transmission and reception of electric power and signals between the electronic endoscope and the processor device, a group of terminals that are typically connected to each other are provided in a connector of each of the electronic endoscope and the processor device, and electric power and signals are transmitted and received through the terminal groups. However, when washing the electronic endoscope, the terminal group of the connector of the electronic endoscope should be waterproof. For this reason, an electronic endoscope has been proposed that performs transmission and reception of electric power and signals in a state of being insulated from the processor device using a pair of coils, a light emitting element and a light receiving element, or the like instead of the terminal group (for example, refer to JP1998-155740A (JP-H10-155740A) and JP2013-208187A).

SUMMARY OF THE INVENTION

An electronic device mounted in the electronic endoscope is exposed to, for example, radiation noise or electrostatic noise of a high-frequency treatment tool that is used together with the electronic endoscope. In the electronic endoscope that performs transmission and reception of electric power and signals in a state of being insulated from the processor device, such as the electronic endoscopes disclosed in JP1998-155740A (JP-H10-155740A) and JP2013-208187A, the terminal group of the connector is eliminated so that waterproof treatment is not necessary. In this case, since the ground of the electronic endoscope floats from the ground of the processor device, there is no way out of noise. Accordingly, there is concern about the malfunction of the electronic device. The invention has been made in view of the aforementioned situation, and it is an object of the invention to provide an electronic endoscope and an electronic endoscope device with increased noise resistance.

According to a first aspect of the invention, there is provided an electronic endoscope including a connector that is connected to a processor device. The connector performs transmission and reception of electric power and signals to and from the processor device. In the connector, an input and output portion for the transmission and reception of electric power and signals is insulated from the processor device, and only a contact portion connected to a ground of the electronic endoscope is electrically connected to a ground of the processor device.

According to a second aspect of the invention, there is provided an electronic endoscope device including: the electronic endoscope according to the first aspect of the invention; and a processor device to which the connector of the electronic endoscope is connected. The processor device performs transmission and reception of electric power and signals to and from the connector.

According to the invention, it is possible to provide an electronic endoscope and an electronic endoscope device with increased noise resistance.

DESCRIPTION OF THE PREFERRED EMBODIMENTS

Hereinafter, a preferred embodiment of the invention will be described with reference to the accompanying drawings.

Figure 1:
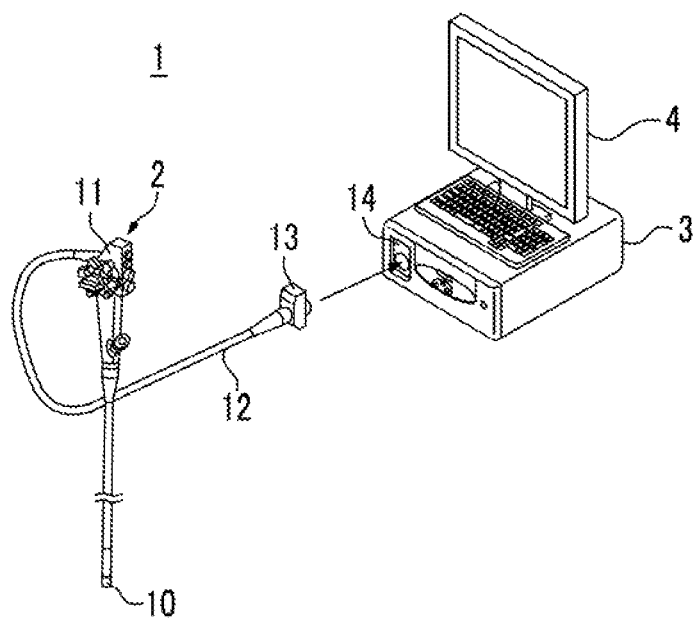
FIG. 1 is an external view of an example of an electronic endoscope device for explaining an embodiment of the invention.

FIG. 1 shows the configuration of an example of an electronic endoscope device for explaining an embodiment of the invention.

An electronic endoscope device 1 includes an electronic endoscope 2, a processor device 3, and a monitor 4 connected to the processor device 3.

The electronic endoscope 2 includes an insertion unit 10 that is inserted into a subject, an operating unit 11 connected to the insertion unit 10, and a universal cord 12 extending from the operating unit 11. A connector 13 is provided at the end of the universal cord 12, and the connector 13 is connected to a connector 14 provided in the processor device 3. The electronic endoscope 2 and the processor device 3 are connected to each other through the connectors 13 and 14.

Figure 2:
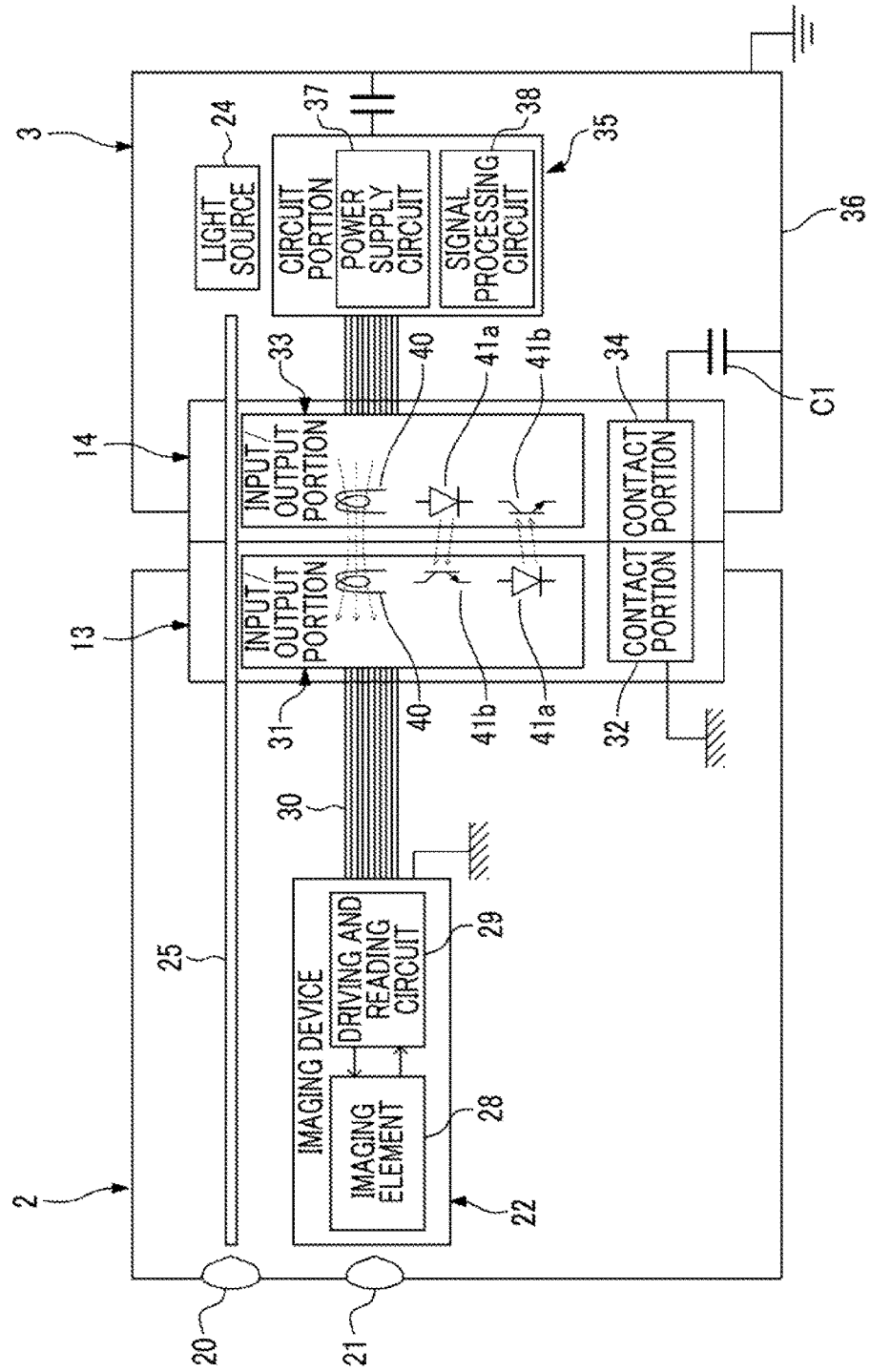
FIG. 2 is a functional block diagram of the electronic endoscope device shown in FIG. 1.

FIG. 2 is a functional block diagram of the electronic endoscope device 1.

An illumination optical system 20 for emitting illumination light, an objective optical system 21, and an imaging device 22 for receiving an image formed by the objective optical system 21 are provided in a tip portion of the insertion unit 10 of the electronic endoscope 2.

The illumination light emitted from the illumination optical system 20 is generated by a light source 24 provided in the processor device 3, and is guided from the light source 24 to the illumination optical system 20 by a light guide 25 provided in the universal cord 12 (refer to FIG. 1).

The imaging device 22 is configured to include an imaging element 28, such as a charge coupled device (CCD) image sensor or a complementary metal oxide semiconductor (CMOS) image sensor, and a driving and reading circuit 29 that drives the imaging element 28 and reads an image signal from the imaging element 28. The driving and reading circuit 29 is configured to include a driver for the imaging element 28, an amplifier for amplifying an image signal read from the imaging element 28, and an AM converter for performing digital conversion of the image signal and outputting the converted image signal, for example.

The operating power of the imaging element 28 and the driving and reading circuit 29 or a control signal input to the driving and reading circuit 29 and an image signal output from the driving and reading circuit 29 are transmitted by a wiring group 30 provided in the universal cord 12, and are transmitted and received between the electronic endoscope 2 and the processor device 3 through the connectors 13 and 14.

An input and output portion 31 for transmission and reception of the power and the signal described above between the connector 13 and a connector 14 of the processor device 3 and a contact portion 32 connected to the ground of the electronic endoscope 2 are provided in the connector 13.

The processor device 3 includes an input and output portion 33, a contact portion 34, and a circuit portion 35.

The input and output portion 33 is provided in the connector 14, and the power and the signal described above are transmitted and received between the input and output portion 33 and the connector 13 of the electronic endoscope 2 connected to the connector 14. The contact portion 34 is also provided in the connector 14, and is connected to a grounded housing (ground) 36 of the processor device 3 through a capacitor C1.

The circuit portion 35 includes a power supply circuit 37 for generating electric power supplied to the imaging element 28 and the driving and reading circuit 29 from a commercial power supply (not shown) and a signal processing circuit 38 for processing the signal of the driving and reading circuit 29, for example. The signal processing circuit 38 is configured to include a control circuit for controlling the operation of the driving and reading circuit 29 and an image processing circuit for generating image data by performing various kinds of signal processing, such as white balance correction, on an image signal, for example. The image data generated by the signal processing circuit 38 is displayed on the monitor 4 (refer to FIG. 1).

The input and output portion 31 of the connector 13 and the input and output portion 33 of the connector 14 perform transmission and reception of electric power and signals therebetween in a state of being insulated from each other. In this specification, "insulation" refers to conductors for transmitting electric power or signals being separated from each other, and the conductors are separated from each other between the input and output portions 31 and 33.

In the example shown in the diagrams, a coil 40 is provided in each of the input and output portions 31 and 33. The pair of coils 40 are disposed opposite each other in a non-contact manner in a state where the connectors 13 and 14 are connected to each other, and electric power is transmitted while maintaining insulation therebetween using electromagnetic induction.

In the input and output portions 31 and 33, a light emitting element 41*a* is provided on the signal output side, and a light receiving element 41*b* is provided on the signal input side. The pair of light emitting element 41*a* and light receiving element 41*b* are disposed opposite each other in a contact or a non-contact manner in a state where the connectors 13 and 14 are connected to each other, and a signal is transmitted while maintaining insulation therebetween using light.

Transmission and reception of electric power and signals performed while maintaining insulation are not limited to the method described above. For example, a magnetic resonance method using the coil 40 as a resonator can be used for transmission and reception of electric power, and radio communication can be used for signal transmission and reception.

On the other hand, the contact portion 32 of the connector 13 and the contact portion 34 of the connector 14 are in contact with each other in a state where the connectors 13 and 14 are connected to each other, and accordingly, the ground of the electronic endoscope 2 and the housing 36 of the processor device 3 are electrically connected to each other.

Since the ground of the electronic endoscope 2 and the housing 36 of the processor device 3 are electrically connected to each other, noise applied to the electronic endoscope 2, such as radiation noise or electrostatic noise of a high-frequency treatment tool, flows from the ground of the electronic endoscope 2 to the housing 36 of the processor device 3. Accordingly, the influence of noise in the electronic endoscope 2 is reduced. In particular, since the housing 36 is grounded in this example, noise is quickly eliminated from the electronic endoscope 2 and the processor device 3. Therefore, it is possible to suppress the malfunction of an electronic device mounted in the electronic endoscope 2, such as the imaging element 28 or the driving and reading circuit 29.

In addition, the capacitor C1 is interposed between the contact portion 34 of the connector 14 and the housing 36 of the processor device 3. Accordingly, the ground of the electronic endoscope 2 is electrically connected to the housing 36 by capacitive coupling in an AC (Alternate current) manner, and floats from the housing 36 in a DC (Direct current) manner. As a result, it is possible to cut a leakage current flowing from the processor device 3 including the power supply circuit 37 to the subject through the electronic endoscope 2 without inhibiting the movement of high-frequency noise to the housing 36.

In addition, the ground of the input and output portion 33 and the ground of the circuit portion 35 including the power supply circuit 37 are also connected to the housing 36 of the processor device 3. However, since the input and output portion 33 is insulated from the electronic endoscope 2, the ground of the input and output portion 33 and the ground of the circuit portion 35 can be common. Therefore, there is no need to separately provide insulation means for insulating the input and output portion 33 and the circuit portion 35 from each other, such as a transformer or a photo coupler.

Although the imaging device 22 (the imaging element 28 and the driving and reading circuit 29) is exemplified as an electronic device mounted in the electronic endoscope 2 in the electronic endoscope device 1 described above, an electronic device mounted in the electronic endoscope 2 is not limited to the imaging device 22. For example, although the electronic endoscope device 1 described above has a configuration in which illumination light generated by the light source 24 of the processor device 3 is guided to the tip portion of the insertion unit 10 of the electronic endoscope 2 by the light guide 25 and is emitted from the illumination optical system 20, it is also possible to provide a light emitting diode (LED) and a driving circuit therefor in the tip portion of the insertion unit 10 and to generate illumination light with the LED.

Figure 3:
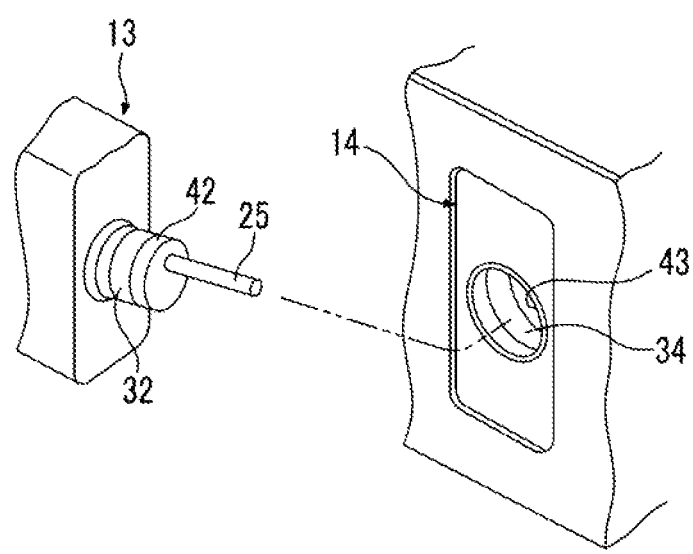
FIG. 3 is a diagram showing the configuration of a connector in each of the electronic endoscope and a processor device shown in FIG. 1.
Figure 4:
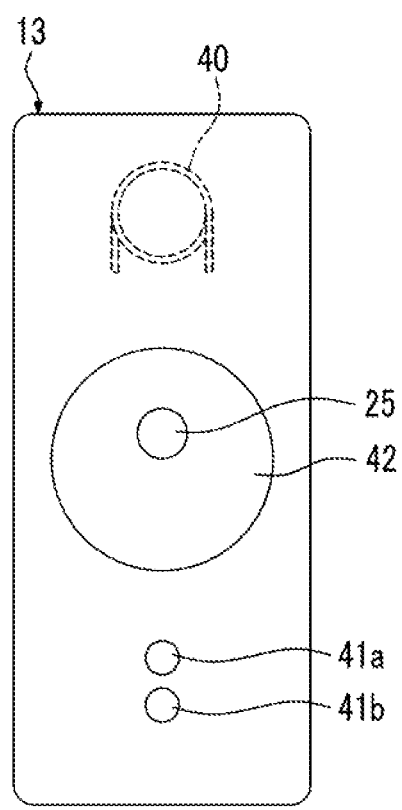
FIG. 4 is a front view of the connector of the electronic endoscope shown in FIG. 3.

FIGS. 3 and 4 show the configuration of the connector 13 of the electronic endoscope 2 and the connector 14 of the processor device 3.

The connector 13 of the electronic endoscope 2 includes a fitting portion 42 formed in a protruding shape, and the connector 14 of the processor device 3 includes a fitting portion 43 formed in a recessed shape. The fitting portions 42 and 43 are fitted to each other by connection of the connectors 13 and 14, and the fitting portion 42 of the connector 13 is covered by the fitting portion 43 of the connector 14.

In the example shown in the diagrams, the protruding fitting portion 42 is provided at the approximate center of the connector 13, and the end of the light guide 25 for guiding the illumination light is held in the fitting portion 42. In addition, the coil 40 for transmission and reception of electric power is provided on one side of both sides of the connector 13 having the fitting portion 42 interposed between both the sides, and the light emitting element 41a and the light receiving element 41b for transmission and reception of a signal are provided on the other side. In addition, the arrangement of the fitting portion 42 in the connector 13 and the arrangement of the light guide 25, the coil 40, the light emitting element 41a, or the light receiving element 41b are not limited to the example shown in the diagrams.

The contact portion 32 of the connector 13 is provided in the fitting portion 42, and the contact portion 34 of the connector 14 connected to the contact portion 32 of the connector 13 is provided in the fitting portion 43. Thus, since the contact portion 32 electrically connected to the housing 36 of the processor device 3 is provided in the protruding fitting portion 42 of the connector 13 covered by the recessed fitting portion 43 of the connector 14, the contact portion 32 is not exposed in a state where the connectors 13 and 14 are connected to each other, that is, during the use of the electronic endoscope device 1. Therefore, since it is possible to prevent the user of the electronic endoscope device 1 from touching the contact portion 32, it is possible to prevent the electric shock of the user.

Preferably, the contact portion 32 is provided on the outer peripheral surface of the fitting portion 42 as in the example shown in the diagram. In this case, since the contact area between the contact portions 32 and 34 can be increased, the ground of the electronic endoscope 2 and the housing 36 of the processor device 3 can be electrically connected to each other more reliably.

As described above, the following matters are disclosed in this specification.

(1) An electronic endoscope including a connector that is connected to a processor device. The connector performs transmission and reception of electric power and signals to and from the processor device. In the connector, an input and output portion for the transmission and reception of electric power and signals is insulated from the processor device, and only a contact portion connected to a ground of the electronic endoscope is electrically connected to a ground of the processor device.

(2) In the electronic endoscope described in (1), the connector includes a fitting portion that fits to the processor device and is covered by the processor device, and the contact portion is provided in the fitting portion.

(3) In the electronic endoscope described in (2), the contact portion is provided on an outer peripheral surface of the fitting portion.

(4) An electronic endoscope device including: the electronic endoscope described in any one of (1) to (3); and a processor device to which the connector of the electronic endoscope is connected. The processor device performs transmission and reception of electric power and signals to and from the connector.

(5) In the electronic endoscope device described in (4), the contact portion of the connector and a ground of the processor device electrically connected to the contact portion are electrically connected to each other by capacitive coupling in an AC manner.

(6) In the electronic endoscope device described in (5), the processor device includes an input and output portion that transmits and receives electric power and signals to and from the input and output portion of the electronic endoscope and a circuit portion that generates the electric power and processes the signal, and a ground of the input and output portion and a ground of the circuit portion are common.

What is claimed is:

1. An electronic endoscope, comprising:
   a connector that is connected to a processor device, the connector performing transmission and reception of electric power and signals to and from the processor device,
   wherein, in the connector, an input and output portion for the transmission and reception of electric power and signals is insulated from the processor device, and only a contact portion connected to a ground of the electronic endoscope is electrically connected to a ground of the processor device,
   wherein the input and output portion includes a coil that transmits electric power using electromagnetic induction and a light receiving element and a light emitting element that transmits signals using light communication, and performs transmission and reception of electric power and signals in the state of being insulated from the processor device,
   wherein the connector includes a fitting portion protruding from the connector on which the contact portion is provided and covers an outer curved circumferential surface of the fitting portion that fits to the processor device and is covered by the processor device.

2. An electronic endoscope device, comprising:
   the electronic endoscope according to claim 1; and
   a processor device to which the connector of the electronic endoscope is connected, the processor device performing transmission and reception of electric power and signals to and from the connector.

3. The electronic endoscope device according to claim 2, wherein the contact portion of the connector and a ground of the processor device electrically connected to the contact portion are electrically connected to each other by capacitive coupling in an AC manner.

4. The electronic endoscope device according to claim 3, wherein the processor device includes an input and output portion that transmits and receives electric power and signals to and from the input and output portion of the electronic endoscope and a circuit portion that generates the electric power and processes the signal, and a ground of the input and output portion and a ground of the circuit portion are common.

5. The electronic endoscope according to claim 1, wherein the fitting portion is formed in a protruding shape and is provided at a center part of the connector.

6. The electronic endoscope according to claim 1, wherein the coil and the light receiving element or the light emitting element are provided on the sides opposite to each other with the contact portion interposed therebetween.

7. The electronic endoscope device according to claim 2, wherein the processor device includes an input and output portion that transmits and receives electric power and signals to and from the input and output portion of the electronic endoscope and a circuit portion that generates the electric power and processes the signal, and
a ground of the input and output portion and a ground of the circuit portion are common.

8. The electronic endoscope according to claim 1, wherein the connector includes the fitting portion protruding from the connector on which the contact portion is provided and covers the outer curved circumferential surface of the fitting portion to increase a contact area of the ground of the electronic endoscope and the ground of the processor device to connect to each other.

* * * * *